(12) United States Patent
Cumpson et al.

(10) Patent No.: US 9,078,628 B2
(45) Date of Patent: Jul. 14, 2015

(54) OFF-MAGNET PATIENT SCAN POSITIONING

(75) Inventors: Patrick T. Cumpson, Chesterland, OH (US); Bradford W. Petot, South Euclid, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 965 days.

(21) Appl. No.: 11/914,951

(22) PCT Filed: May 1, 2006

(86) PCT No.: PCT/IB2006/051357
§ 371 (c)(1),
(2), (4) Date: Nov. 20, 2007

(87) PCT Pub. No.: WO2006/126108
PCT Pub. Date: Nov. 30, 2006

(65) Prior Publication Data
US 2008/0194942 A1 Aug. 14, 2008

Related U.S. Application Data

(60) Provisional application No. 60/684,349, filed on May 25, 2005.

(51) Int. Cl.
| | | |
|---|---|---|
| A61B 5/00 | (2006.01) | |
| A61B 5/055 | (2006.01) | |
| A61B 6/04 | (2006.01) | |
| A61B 6/00 | (2006.01) | |

(52) U.S. Cl.
CPC ............... *A61B 5/704* (2013.01); *A61B 5/0555* (2013.01); *A61B 6/04* (2013.01); *A61B 6/0407* (2013.01); *A61B 6/469* (2013.01)

(58) Field of Classification Search
CPC ........ A61B 5/704; A61B 5/055; A61B 6/469; A61B 6/0407; A61B 6/04
USPC ............ 5/81.1 HS, 600, 601; 108/20; 378/20, 378/57, 208, 209; 414/749.1; 198/832.1; 600/415
See application file for complete search history.

(56) References Cited

U.S. PATENT DOCUMENTS

| | | | |
|---|---|---|---|
| 4,105,923 A | | 8/1978 | Hynes |
| 4,117,337 A | * | 9/1978 | Staats ............................. 378/17 |
| 4,131,802 A | | 12/1978 | Braden et al. |
| 4,727,328 A | * | 2/1988 | Carper et al. ................. 324/318 |
| 5,077,843 A | * | 1/1992 | Dale et al. ......................... 5/600 |
| 5,197,474 A | | 3/1993 | Englund et al. |
| 5,204,629 A | | 4/1993 | Ueyama |
| 5,259,011 A | | 11/1993 | Petro |

(Continued)

FOREIGN PATENT DOCUMENTS

DE        10151236 A1    5/2003

*Primary Examiner* — Nicholas Polito (57) ABSTRACT

To position an imaging subject (16) in an imaging or therapy system (10), the imaging subject (16) is arranged on a linearly translatable tabletop (26) disposed on a movable trolley (30). A position of a region of interest (24) of the imaging subject along the linearly translatable tabletop is selected using an elongated position selector (40, 40', 40") that is elongated in a translation direction (z) of the linearly translatable tabletop (26). After the selecting, the movable trolley is docked with the imaging or therapy system (10). After the docking, the tabletop is linearly translated to move the imaging subject to the imaging or therapy system, the amount of linear translating being based on the selected position of a region of interest along the linearly translatable tabletop.

14 Claims, 6 Drawing Sheets

(56) References Cited

U.S. PATENT DOCUMENTS

| | | | |
|---|---|---|---|
| 5,491,849 A * | 2/1996 | Colussi et al. | 4/559 |
| 6,424,855 B1 | 7/2002 | Blasche et al. | |
| 6,460,206 B1 * | 10/2002 | Blasche et al. | 5/601 |
| 6,973,689 B2 * | 12/2005 | Lenting et al. | 5/601 |
| 7,174,587 B2 * | 2/2007 | Tybinkowski et al. | 5/601 |
| 2005/0020906 A1 * | 1/2005 | Seijger et al. | 600/415 |

* cited by examiner

OFF-MAGNET PATIENT SCAN POSITIONING

CROSS REFERENCE TO RELATED APPLICATIONS

This application claims the benefit of U.S. provisional application Ser. No. 60/684,349 filed May 25, 2005, which is incorporated herein by reference.

The following relates to the medical imaging arts. It finds particular application in magnetic resonance imaging (MRI), and will be described with particular reference thereto. However, it also finds application in magnetic resonance spectroscopy, positron emission tomography (PET) imaging, single-photon emission computed tomography (SPECT) imaging, computed tomography (CT) imaging, radiation therapy, and other imaging and therapeutic modalities in which a patient or other imaging subject is aligned with an imaging or therapeutic system.

Medical imaging or therapy typically targets a region of interest, such as the heart, lungs, brain, arm, leg, torso, or, in some cases, the whole body. For radiation therapy, a cancerous organ is typically targeted. The MRI scanner or other medical apparatus used to perform the imaging or therapy is typically stationary, and images or otherwise operates upon a fixed volume or slice in space. In MRI, the position of the imaging slice or volume is typically specified by an isocenter of the MRI scanner; however, another spatial reference could be used. To image or otherwise operate upon the region of interest of the imaging subject, that region of interest must be disposed in the imaging volume or slice. Thus, a preliminary operation in MRI imaging workflow is to dispose the region of interest at the imaging volume or slice.

In some existing patient positioning systems, a fixed patient couch extends away from the bore of the scanner. The couch includes a linearly translatable tabletop that can be moved in and out of the bore using a drive motor or other calibrated translation system. The patient lies down or is otherwise disposed on the tabletop, and is moved toward the scanner bore. An alignment laser beam having a predetermined spatial relationship with the isocenter of the MRI scanner, such as being at an entrance to the scanner bore, is directed onto the patient. The translatable tabletop is moved by or under the direction of the radiologist or other scanner operator until the region of interest of the patient is located at the alignment laser. The radiologist or other scanner operator presses a push-button or otherwise indicates that the tabletop position is now aligned. The drive motor then moves the region of interest of the patient to the isocenter of the bore based on the predetermined spatial relationship with the bore isocenter and the laser position.

In some cases, the patient couch is a wheeled detachable couch. The patient lies down or is otherwise disposed on the tabletop of the movable couch, which is then rolled over to the MRI scanner and docked with the MRI scanner using a suitable mechanical docking arrangement. Once docked, the wheeled couch is in effect attached or fixed to the MRI scanner, and the alignment proceeds with reference to the alignment laser beam as in the case of a fixed couch.

These existing patient positioning approaches have certain disadvantages. Because the couch must be fixed or docked with the MRI before patient positioning can commence, the radiologist or other scanner operator is in close proximity to the magnet, which raises concerns about possible overexposure of the operator to strong magnetic fields in the vicinity of the magnet. Similar concerns may arise in other imaging or therapeutic modalities, such as CT or radiation therapy, where operator exposure to radiation may be a concern.

Moreover, alignment at the magnet can adversely affect patient throughput of the MRI scanner. In the case of a fixed couch, all patient preparation including patient positioning must be performed at the magnet, which means that only one patient can be being prepared for imaging or imaged at any given time. In the case of a wheeled detachable couch, most patient preparation can be performed away from the magnet, allowing imaging of one patient while the next patient to be imaged is being prepared. However, even with a wheeled detachable couch, the patient positioning is performed at the magnet, which can limit the patient throughput.

Still further, alignment at the magnet can be uncomfortable and intimidating for the patient. The patient is usually nervous about the impending MRI imaging procedure, and the large magnet of the MRI scanner and the narrow magnet bore can be unnerving. Using existing patient positioning approaches, the patient is delayed at the entrance to the magnet bore while the positioning is performed, allowing patient anxieties to build. Moreover, the alignment involves moving the patient via the motorized tabletop to align the patient with the alignment laser beam. Depending upon the skill of the radiologist or other scanner operator, this alignment could involve moving the patient back and forth several times to attain precise alignment with the laser beam. Such movement can be uncomfortable for the patient.

The present invention contemplates improved apparatuses and methods that overcome the aforementioned limitations and others.

According to one aspect, a positioning system for an imaging or therapy system is disclosed. A linearly translatable tabletop is arrangeable to translate an imaging subject disposed on the tabletop to the imaging or therapy system. An elongated position selector is elongated in a translation direction of the linearly translatable tabletop. The elongated position selector enables selection of a position of a region of interest of the imaging subject along the linearly translatable tabletop.

According to another aspect, a positioning method is disclosed for positioning an imaging subject in an imaging or therapy system. The imaging subject is arranged on a linearly translatable tabletop. A position of a region of interest of the imaging subject along the linearly translatable tabletop is selected. The selecting does not require moving the linearly translatable tabletop. The tabletop is linearly translated to move the imaging subject to the imaging or therapy system, the amount of linear translating being based on the selected position of the region of interest along the linearly translatable tabletop.

According to another aspect, a positioning method is disclosed for positioning an imaging subject in an imaging or therapy system. The imaging subject is arranged on a linearly translatable tabletop disposed on a movable trolley. A position of a region of interest of the imaging subject is designated on one of the linearly translatable tabletop and the trolley. After the selecting, the movable trolley is docked with the imaging or therapy system. After the docking, the tabletop is linearly translated to move the imaging subject to the imaging or therapy system, the amount of linear translating being based on the designated position of the region of interest.

One advantage resides in reduced exposure of the radiologist or other operator to magnetic fields, radiation, or other adverse environmental aspects of the MRI scanner, radiation system, or so forth.

Another advantage resides in improved patient throughput by allowing one patient to be imaged while the next patient is prepared and positioned.

Another advantage resides in a reduced delay period during which the patient is at the magnet awaiting an impending imaging or therapeutic procedure.

Another advantage resides in positioning the patient while the patient remains stationary.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

Figure 1:
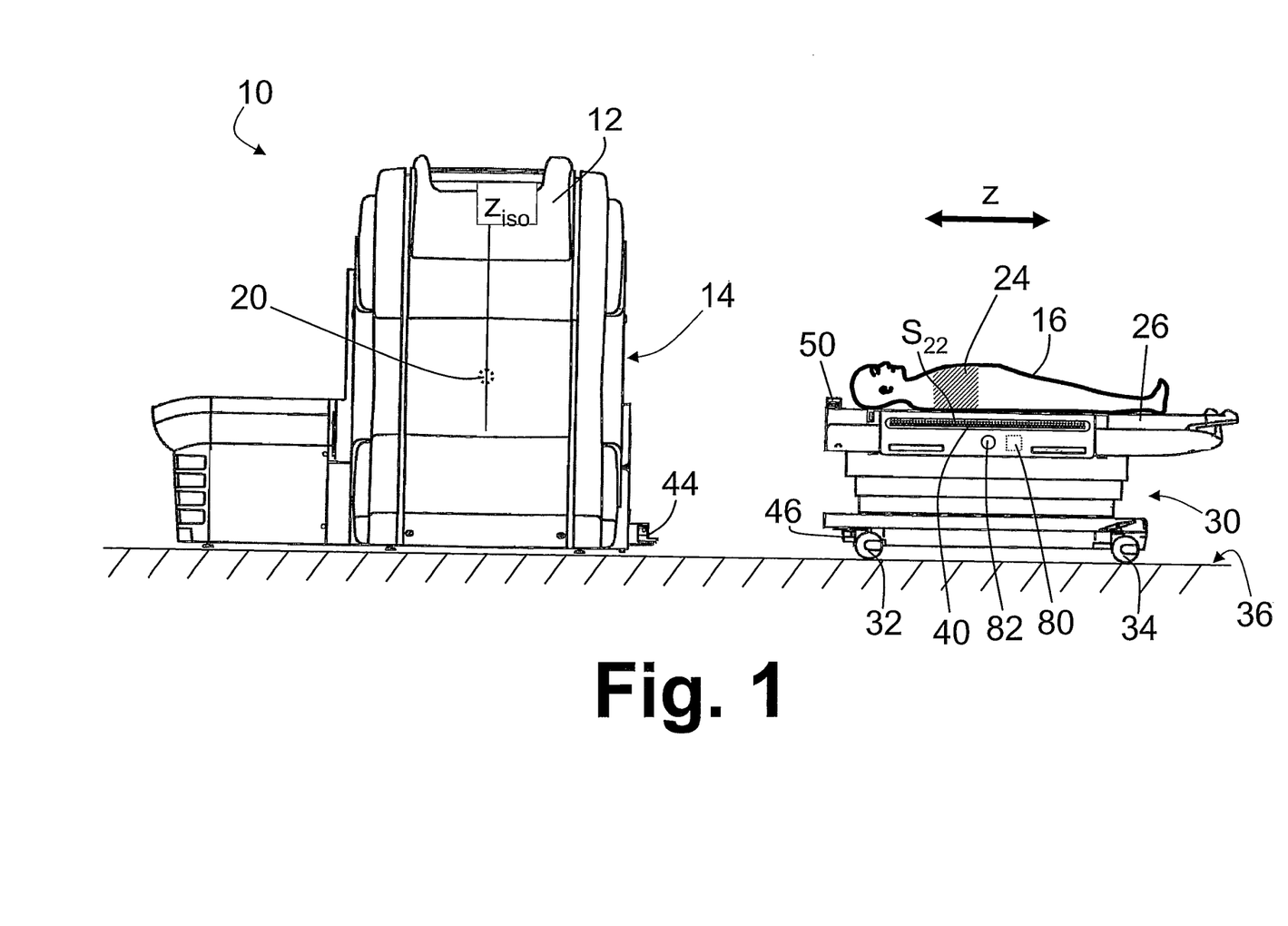
FIG. 1 diagrammatically shows an MRI scanner and a trolley, with the trolley undocked from the MRI scanner and supporting a patient being prepared for imaging away from the MRI scanner.
Figure 2:
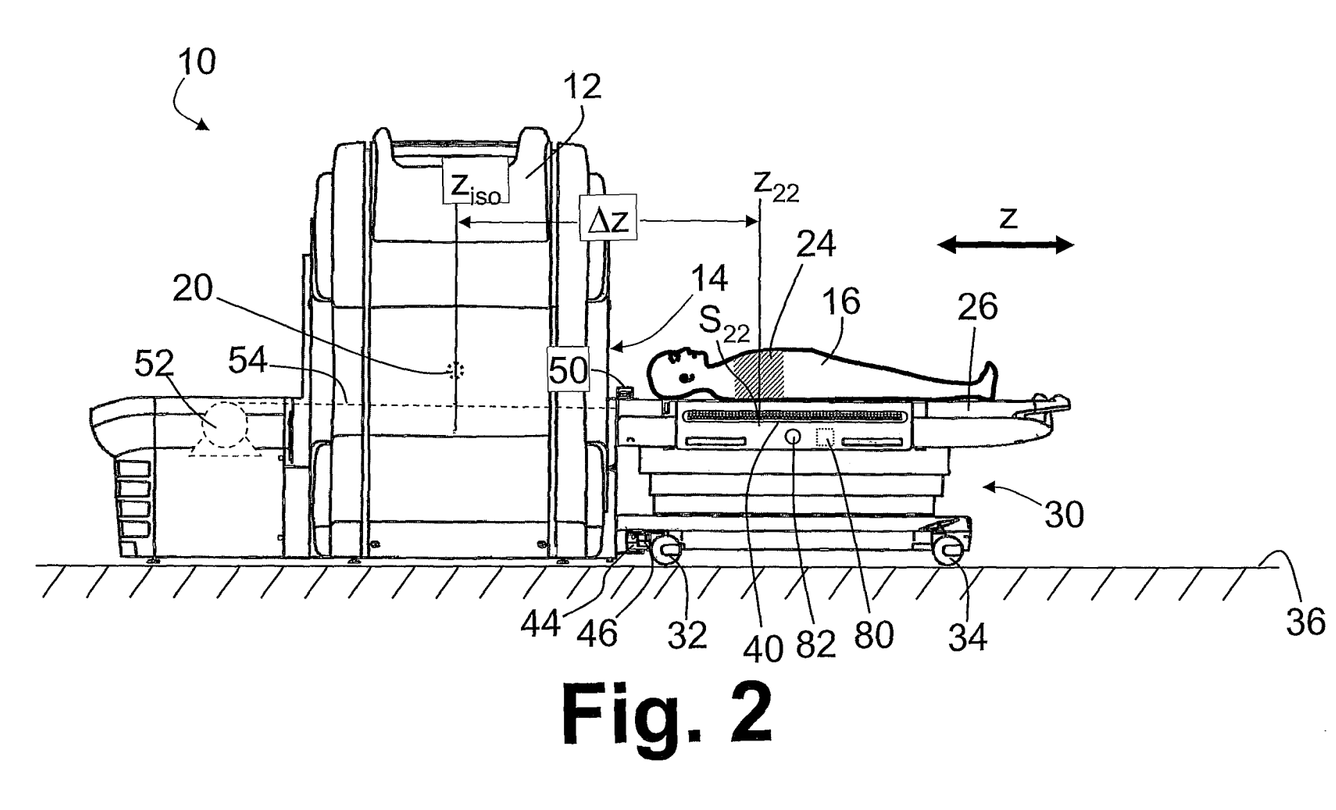
FIG. 2 diagrammatically shows the MRI scanner and the trolley, with the trolley supporting the patient and docked with the MRI scanner.

With reference to FIGS. 1 and 2, a magnetic resonance imaging scanner 10 includes a housing 12 that encloses components including at least a main magnet, magnetic field gradient coils, and one or more radio frequency coils (housed components not shown). The main magnet is preferably superconducting and cryoshrouded. The housing 12 defines a bore 14 inside which a subject is placed for imaging. The magnetic field gradient coils for spatially encoding the magnetic resonance signals are enclosed in the housing 12 or are arranged in the bore 14, as are one or more radio frequency coils and other optional components that are cooperatively used to generate, tailor, and detect magnetic resonance signals of the imaging subject.

In MRI, a patient 16 or other imaging subject is disposed in the bore 14 of the main magnet, where the main magnet produces a static main magnetic field through the imaging subject. The radio frequency coils or antennae inject radio frequency power or pulses into the imaging subject so as to excite magnetic resonances in the imaging subject 16, which are detected by the same or different radio frequency coils or antennae. The magnetic field gradient coils superimpose onto the static magnetic field one or more selected magnetic field gradients in the imaging subject so as to spatially encode and/or localize the magnetic resonances. Suitable reconstruction processing is performed to decode the spatial encoding so as to produce a magnetic resonance image of the imaging subject. Optionally, the MRI scanner 10 is also selectively configurable to perform magnetic resonance spectroscopy.

The main magnet and magnetic field gradient coils are configured to image a selected region disposed at an isocenter 20 of the scanner 10. The isocenter 20 is diagrammatically indicated in FIGS. 1 and 2 by a small dotted circle; however, it is to be appreciated that the isocenter 20 is located inside the housing 12 and thus is generally not visible from outside the housing 12. Moreover, the isocenter 20 is a conceptual point defined in space, and does not coincide with any physical structure.

To image a region of interest 24 of the imaging subject 16, that region of interest 24 should be positioned at the isocenter 20 of the scanner 10. The imaging subject is initially disposed on a tabletop 26 supported by a movable trolley 30 that is movable on wheels, rollers 32, 34, or the like across the floor 36. The tabletop 26 is linearly translatable in a direction z of linear translation. In some embodiments, the tabletop 26 is locked down in a designated initial position when the patient 16 is placed onto the tabletop 26. In other embodiments, the tabletop 26 is locked down in an arbitrary initial position when the patient 16 is placed onto the tabletop 26, and the initial position is stored or otherwise indexed, for example respective to a designated reference position of the tabletop 26.

Figure 3:
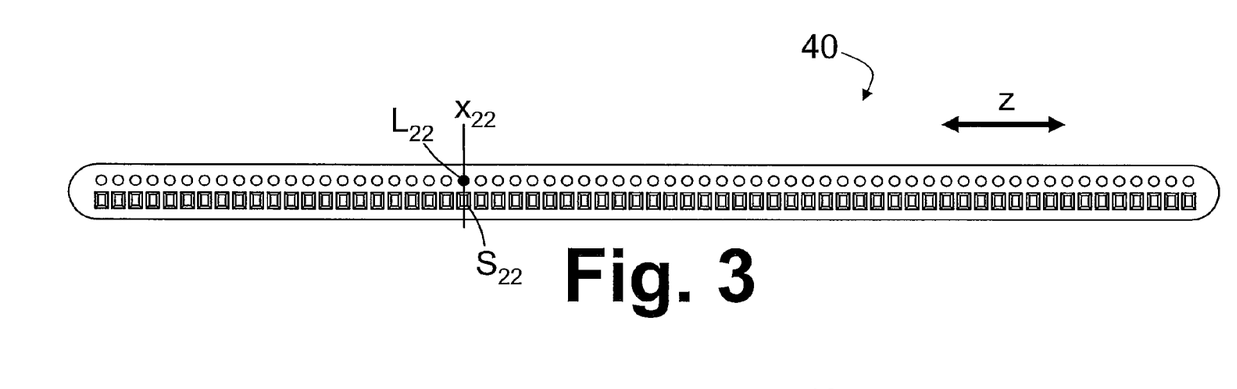
FIG. 3 shows the elongated position selector of the trolley of FIGS. 1 and 2.
Figure 4:
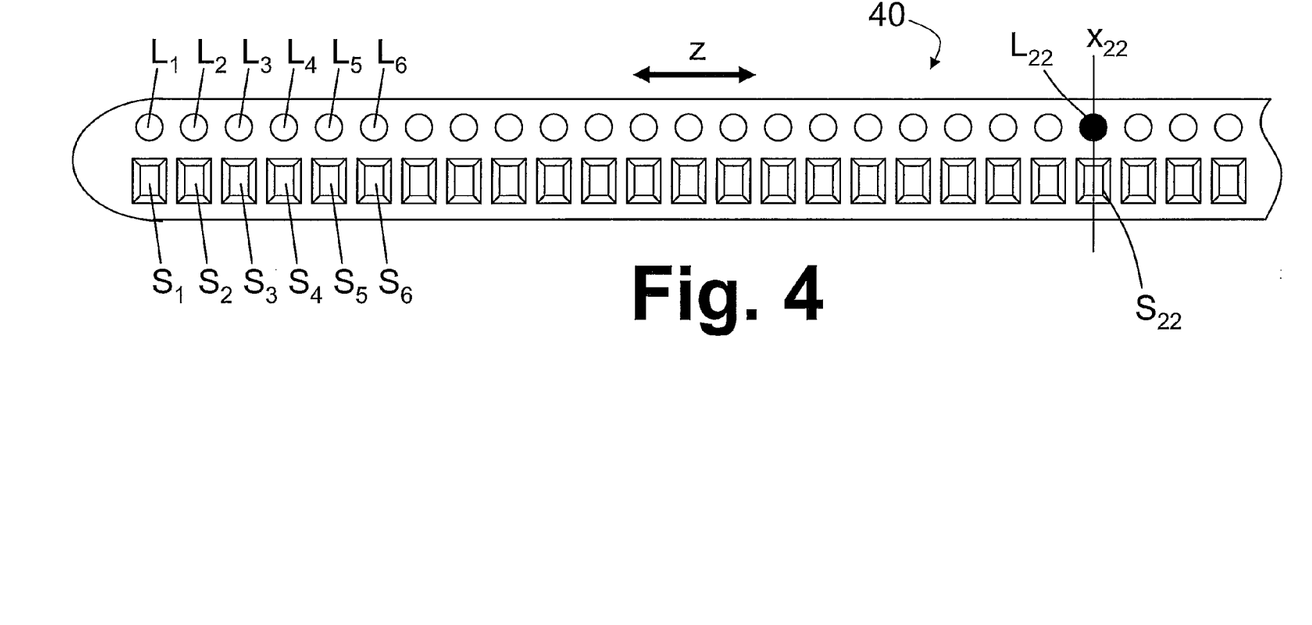
FIG. 4 shows an enlarged view of the left-most 25 discrete push-button selectors of the elongated position selector of FIG. 3.

With continuing reference to FIGS. 1 and 2, and with further reference to FIGS. 3 and 4, an elongated position selector 40 is mounted on the trolley 30. The elongated position selector 40 is stationary respective to the trolley 30, and does not translate when the tabletop 26 is linearly translated in the translation direction z. Alternatively, the selector could be mounted on the tabletop and the position of the tabletop relative to the trolley noted. The elongated position selector 40 is elongated in the translation direction z of the linearly translatable tabletop 26. In the embodiment of FIGS. 1-4, the elongated position selector 40 includes an array of discrete selectors, the first six discrete selectors $S_1$, $S_2$, $S_3$, $S_4$, $S_5$, $S_6$ and the twenty-second discrete selector $S_{22}$ being labeled in FIG. 4. As seen in FIG. 3 which shows the entire elongated position selector 40, the illustrated elongated position selector 40 includes an array of sixty-four discrete selectors at a spacing of about one centimeter between neighboring selectors. FIG. 4 shows a close-up view including only the first twenty-five of the sixty-four discrete selectors. Although the discrete selectors are shown evenly spaced in FIGS. 1-4, in some embodiments the discrete selectors may be spaced closer together in regions such as the head where high positioning precision is called for, and spaced further apart in regions where lower positioning precision is acceptable.

In the embodiment shown in FIGS. 1-4, each of the discrete selectors $S_1$, $S_2$, $S_3$, $S_4$, $S_5$, $S_6$, and so forth is a sealed membrane push-button. Sealed push-buttons have advantages such as being easily cleaned, and being sealed against contamination by fluids, dust, or so forth. However, the discrete selectors can be toggle switches, levers, or other devices. Since activation of a push-button is not readily visually apparent, each of the discrete selectors $S_1$, $S_2$, $S_3$, $S_4$, $S_5$, $S_6$, and so forth has an associated discrete indicator lamp $L_1$, $L_2$, $L_3$, $L_4$, $L_5$, $L_6$, and so forth, respectively. The discrete indicator lamps can be light emitting diodes (LEDs), miniature incandescent lamps, or so forth. While the associated discrete indicator lamps are physically separated from the discrete selectors in the embodiment of FIGS. 1-4, it is also contemplated to use discrete push-button selectors having the indicator lamps integrated with the push-buttons. Moreover, if the discrete selectors are toggle switches, levers, or another selector whose activation and deactivation is readily visually apparent, then the indicator lamps can optionally be omitted.

Each discrete selector of the array of discrete selectors $S_1$, $S_2$, $S_3$, $S_4$, $S_5$, $S_6$, and so forth is positioned at a designated position along the translation direction z. To select the position of the region of interest 24 of the imaging subject 16 along the linearly translatable tabletop 26, the radiologist operates the discrete selector at that position. In the illustrated example of FIGS. 1-4, the discrete push-button $S_{22}$ happens to coincide with the position of the region of interest 24; hence, the radiologist presses the discrete push-button $S_{22}$ causing the corresponding indicator lamp $L_{22}$ to light up. The discrete selectors $S_1$, $S_2$, $S_3$, $S_4$, $S_5$, $S_6$, and so forth are preferably electrically interconnected such that selection of one of the discrete selectors deselects the other discrete selectors. Hence, for example, if the radiologist first pressed the discrete selector push-button $S_4$ causing the indicator lamp $L_4$ to light up, and then pressed the discrete push-button $S_{22}$, the latter pressing of the discrete push-button $S_{22}$ would deselect the selector $S_4$ causing the indicator lamp $L_4$ to turn off and would select the discrete push-button $S_{22}$ to light up the corresponding indicator lamp $L_{22}$.

In some embodiments, matched elongated selectors extend along each side of the patient. Activating one of the discrete pushbuttons causes the corresponding indicator lamps on both sides of the patient to illuminate. The pair of illuminated indicator lamps define a transverse plane.

The selection of the region of interest 24 using the elongated position selector 40 can be done with the movable trolley 30 positioned away from the MRI scanner 10. For example, it may be advantageous to prepare the patient 16, including positioning the patient with suitable comfort items such as pillows, installing local radio frequency coils, and selecting the region of interest 24, in another room or at a sufficient distance away from the MRI scanner 10 to avoid exposure of the radiologist to magnetic fields produced by the MRI scanner 10. Moreover, if two or more movable trolleys are provided, then one patient can be imaged while the next patient is being prepared for imaging on a different trolley.

With continuing reference to FIGS. 1 and 2, once the patient preparation including selection of the region of interest 24 is complete, the movable trolley 30 is docked with the MRI scanner 10. Docking is achieved using a suitable docking member 44 on the MRI scanner 10 that mates with a corresponding docking member 46 on the movable trolley 30. The docking positions the trolley 30 at a fixed position respective to the MRI scanner 10. In some embodiments, the docking automatically provides electrical and communication connections. In other embodiments, one or more separate connectors are used to establish electrical and communication connection.

As a consequence of the docking, the elongated position selector 40 has a predetermined position respective to the isocenter 20 of the MRI scanner 10 when the trolley 30 is docked. In FIG. 2, the position of the isocenter 20 along the translation direction z is designated as $z_{iso}$. The position of the activated selector $S_{22}$ along the translation direction z with the trolley 30 docked is designated as $Z_{22}$. Since the elongated position selector 40 has a predetermined spatial relationship with the MRI scanner 10 (and more particularly with the isocenter 20) when the trolley 30 is docked, it follows that a separation distance $\Delta z$ along the translation direction z between the position $z_{iso}$ of the isocenter 20 and the position $Z_{22}$ of the activated selector $S_{22}$ is known. For example the separation distance $\Delta z$ for each of the discrete selectors $S_1$, $S_2$, $S_3$, $S_4$, $S_5$, $S_6$, and so forth when the trolley 30 is docked can be tabulated and stored in memory. If the elongated position selector is positioned on the movable tabletop rather than on the trolley, then the separation distance $\Delta z$ should take into account the offset of the tabletop position (if any) relative to the docked trolley.

Thus, the separation distance $\Delta z$ along the translation direction z between the position $z_{iso}$ of the isocenter 20 and the position of the region of interest 24 is known to be $\Delta z$. Accordingly, the tabletop 26 is linearly translated by a distance $\Delta z$ along the translation direction z to move the selected region of interest 24 to the isocenter 20 of the MRI scanner 10. In some embodiments, a coil coupling element 50 couples local coils disposed on the tabletop 26 with the MRI scanner 10. In the illustrated embodiment, a drive motor 52 and coupling belt, cabling, shafts 54 or so forth (diagrammatically shown in phantom in FIG. 2) disposed in or on the MRI scanner 10 mechanically couples with the tabletop 26 to enable calibrated linear translation of the tabletop into the bore 14 of the MRI scanner 10. In other embodiments, the calibrated translation motive system may be built into the trolley 30. In yet other embodiments, components of the motive system are disposed in each of the MRI scanner 10 and the trolley 30.

Figure 5:
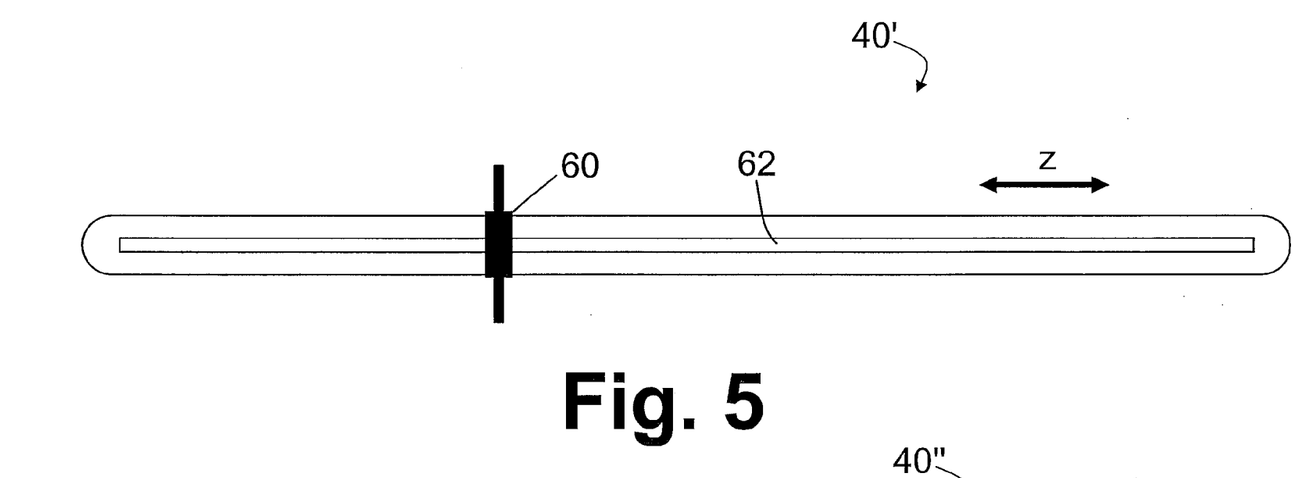
FIG. 5 shows an alternative elongated position selector which employs a slider for marking the position of the region of interest along the tabletop.
Figure 6:
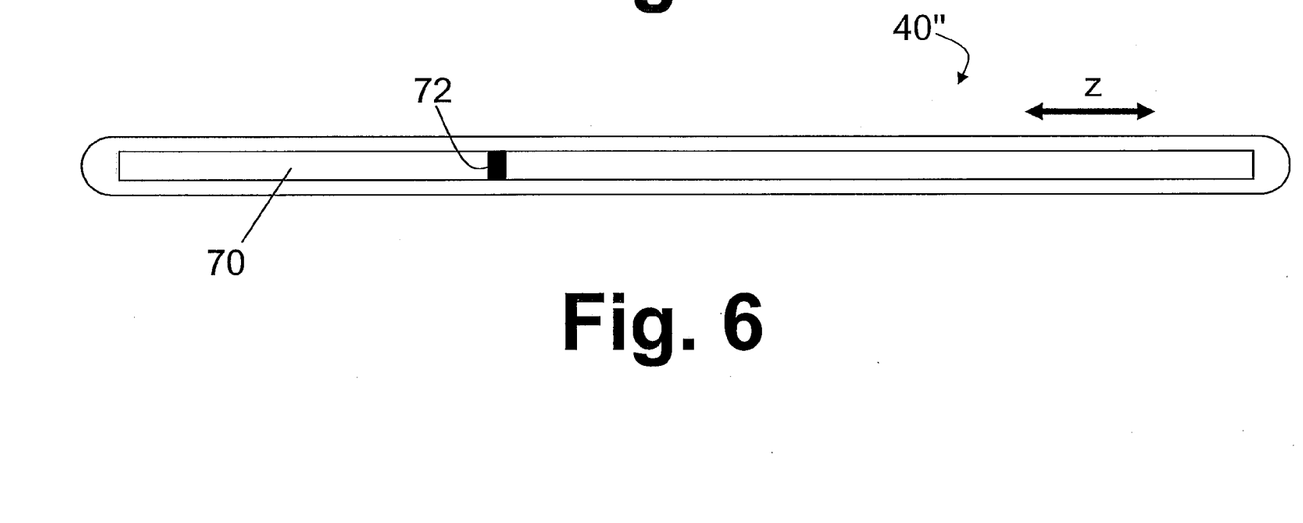
FIG. 6 shows an alternative elongated position selector which employs a touch-sensitive screen for marking the position of the region of interest along the tabletop.

With reference to FIGS. 5 and 6, the elongated position selector 40 can take other physical forms. FIG. 5 shows an alternative elongated position selector 40' that uses a slider 60 that is movable along a track 62 arranged parallel with the tabletop 26. The position of the slider 60 along the track 62 selects the position of the region of interest 24 along the linearly translatable tabletop 26. FIG. 6 shows another alternative elongated position selector 40" that uses an elongated touch-sensitive screen 70 that produces a light or mark 72 at the last position where the radiologist touched the screen 70. The position of the last touch mark 72 along the elongated touch-sensitive screen 70 selects the position of the region of interest 24 along the linearly translatable tabletop 26.

The elongated position selectors 40, 40', 40" are illustrative examples; other elongated position selectors can be used. For example, a trackball or dial, either on the trolley or at another location, can be used to index the illuminated indictor lamp, and hence the selected location. In order to provide advantageous correspondence between a position along the elongated position selector 40, 40', 40" and the position of the region of interest 24, the elongated position selector 40, 40', 40" should span the range of likely positions of the region of interest 24 along the translation direction z. In some embodiments, the elongated position selector 40, 40', 40" has a length in the direction of elongation of at least 0.3 meter, which is suitable if the region of interest is always the same part of the anatomy, such as the head. In some other embodiments, the elongated position selector 40, 40', 40" has a length in the direction of elongation of at least 0.7 meter, which is suitable if the region of interest includes a larger span of the anatomy. In yet some other embodiments, the elongated position selector 40, 40', 40" has a length in the direction of elongation of at least one meter, which is long enough to substantially span the body of most patients from head to toe with some selective positioning of the patient 16 on the tabletop 26.

One issue with the elongated position selector 40, 40', 40" is that its elongated nature parallel with the tabletop 26 makes it relatively easy to accidentally bump the selector, for example when the trolley 30 is rolled over to the MRI scanner 10, and thus inadvertently change the selected position. In one approach for addressing this problem, a storage 80 is disposed on the movable trolley for storing the selection of the position of the region of interest. The storage 80 is diagrammatically indicated in FIGS. 1 and 2, and is suitably embodied as an electronic memory such as a random access memory (RAM) or flash memory, a data register on a microprocessor or microcontroller, or so forth. For the elongated position selector 40 having sixty-four discrete selector push-buttons, it will be recognized that since $64=2^6$ a six-bit register is sufficient to store the position selection; hence, a microprocessor or microcontroller data register is sufficient to store the selected position of the region of interest. The user can load the currently selected position setting of the elongated position selector 40 into the storage 80 by, for example, pressing a "Store Position" button 82. To further assure that the position is not inadvertently changed during movement of the trolley 30, the "Store Position" button 82 can be recessed, include a cover plate, or be otherwise protected from inadvertent activation. The storage 80 optionally also stores calibration data, such as a calibration table of separations between each discrete selector and the bore isocenter 20 with the trolley 30 docked, a spacing between discrete selectors coupled with a separation between a reference discrete selector and the bore isocenter 20 when the trolley 30 is docked (from which the separations of all other discrete selectors can be calculated, assuming uniform spacing between selectors), and so forth.

Figure 7:
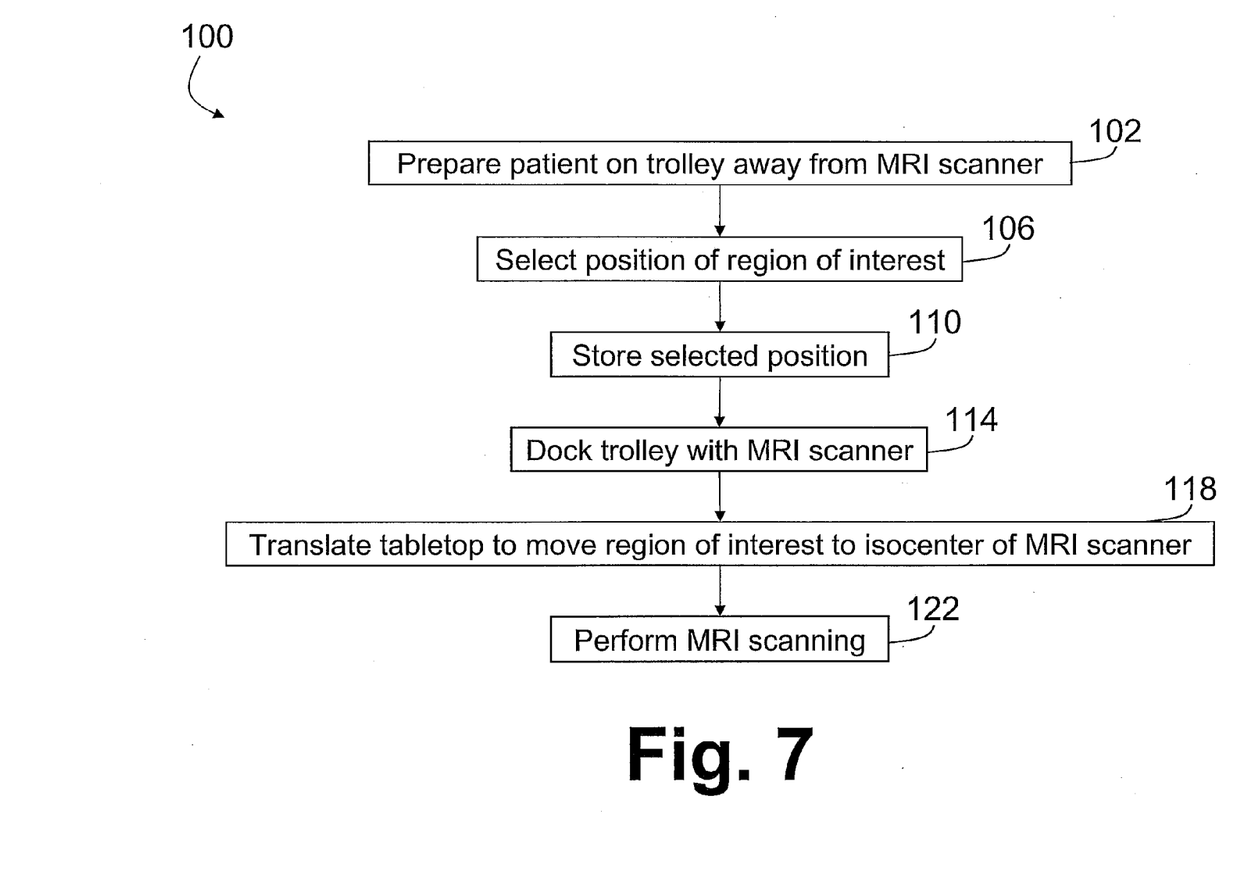
FIG. 7 shows a patient positioning method suitably performed in conjunction with the trolley of FIGS. 1 and 2.

With reference to FIG. 7, a suitable patient positioning method 100 employing the elongated position selector 40, 40', 40" begins by a preparation operation 102. The preparation operation typically includes locking down the tabletop 26, verifying patient identification, arranging the patient 16 on the tabletop 26 optionally using pillows or other comfort devices, and mounting optional local radio frequency coils on the tabletop 26 proximate to the patient 16. With the patient arranged on the tabletop 26, the elongated position selector 40, 40', 40" is used to perform a selection 106 of the region of interest 24 of the patient 16. Typically, the radiologist will visually determine the position of the region of interest 24, and select the closest discrete selector of the elongated position selector 40. If the elongated position selector 40' is used, the slider 60 is moved to the visually determined position of interest 24. If the elongated position selector 40" is used, the radiologist touches the touch screen 70 to mark the visually determined position of interest 24. The selected position is stored in a storage operation 110, for example by activating the "Store Position" button 82 of the trolley 30 to store the position in the storage 80.

The trolley 30 is then docked 114 with the MRI scanner 10 using the docking members 44, 46. The radiologist then initiates translation 118 of the tabletop 26 to move the selected region of interest 24 to the isocenter 20 of the MRI scanner 10. This process can be initiated by pressing a suitable button, via control software of the MRI scanner 10, or so forth. The translation 118 moves the tabletop 26, and hence the patient 16, the distance Δz corresponding to the distance between the position $Z_{iso}$ of the isocenter 20 and the position of the selected region of interest 24 stored in the storage 80. Optionally, the storing operation 110 is omitted, in which case the translation 118 moves the tabletop 26 the distance Δz corresponding to the distance between the position $Z_{iso}$ of the isocenter 20 and the position currently selected by the elongated position selector 40, 40', 40". With the region of interest 24 positioned at the isocenter 20 of the MRI scanner 10, MRI scanning is performed in operation 122.

In the flowcharted method 100, the preparatory operations 102, 106, 110 are performed with the trolley 30 positioned away from the MRI scanner 10, such as in a preparatory room or alcove. Alternatively, the trolley 30 can be docked before performing the positioning operations 106, 110.

Figure 8:
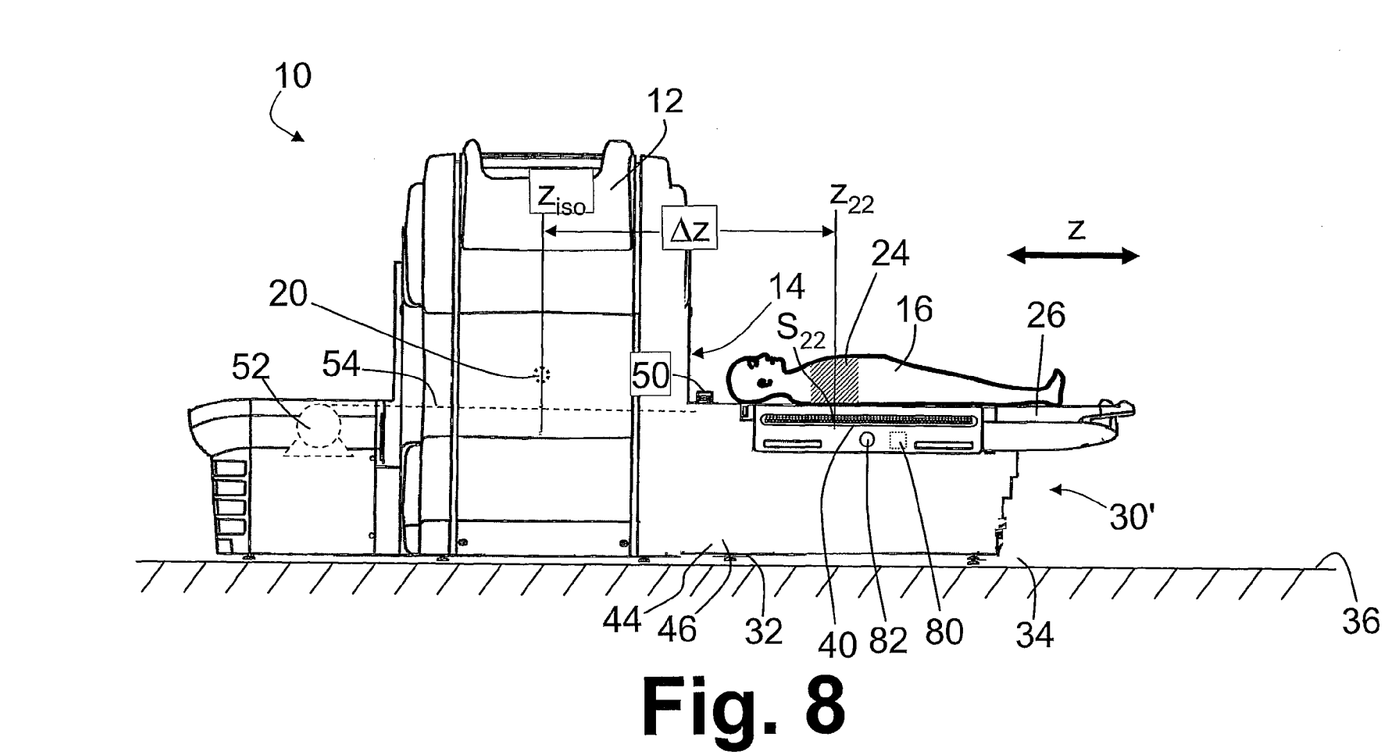
FIG. 8 diagrammatically shows the MRI scanner with a fixed patient couch attached thereto, the couch supporting a patient being prepared for imaging.

With reference to FIG. 8, in some embodiments, the trolley 30 is replaced by a stationary couch 30' that is permanently connected with the MRI scanner 10. The fixed couch 30' supports the linearly translatable tabletop 26 and the elongated position selector 40, with the elongated position selector 40 being stationary relative to the stationary couch 30' and thus having a predetermined fixed spatial relationship with the MRI scanner 10. Employing the elongated position selector 40, 40', 40" with the fixed couch 30' provides the benefit of allowing the position of the region of interest 24 to be selected without moving the patient 16 back and forth respective to an alignment laser beam or other fixed alignment point.

The elongated position selector 40, 40', 40" and associated patient positioning methods have been described with reference to the example MRI scanner 10 and the example MRI scanning application. However, it will be appreciated that the elongated position selector 40, 40', 40" is readily used for patient positioning in conjunction with other imaging or therapy systems in which the patient or other imaging subject is to be aligned with the imaging or therapeutic system. For example, the elongated position selector 40, 40', 40" is readily used for patient positioning in conjunction with magnetic resonance spectroscopy, positron emission tomography (PET) imaging, single-photon emission computed tomography (SPECT) imaging, computed tomography (CT) imaging, radiation therapy, and so forth.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A positioning system for an imaging or therapy system, the positioning system comprising:
   a linearly translatable tabletop arranged to linearly translate an imaging subject disposed on the tabletop toward or away from the imaging or therapy system; and
   an elongated position selector that is elongated in a translation direction of the linearly translatable tabletop, the elongated position selector enabling selection of a position of a region of interest of the imaging subject along the linearly translatable tabletop, the elongated position selector not mounted on the linearly translatable tabletop and not linearly translating with the linearly translatable tabletop as the linearly translatable tabletop is linearly translated toward or away from the imaging or therapy system, wherein the elongated position selector comprises:
   a linear array of discrete selectors arranged parallel with the tabletop.

2. The positioning system as set forth in claim 1, wherein the elongated position selector has a length in the direction of elongation of at least 0.3 meter.

3. The positioning system as set forth in claim 1, wherein the elongated position selector has a length in the direction of elongation of at least 0.7 meter.

4. The positioning system as set forth in claim 1, wherein the elongated position selector has a length in the direction of elongation of at least one meter.

5. The positioning system of claim 1, further comprising:
   storage for storing the selection of the position of the region of interest; and
   a selector that, when selected, causes the current selection of the position of the region of interest to be stored in the storage.

6. The positioning system of claim 1, wherein the discrete selectors include sealed membrane push-buttons.

7. The positioning system of claim 1, wherein the discrete selectors are electrically interconnected such that selection of one of the discrete selectors deselects the other discrete selectors.

8. A positioning system for an imaging or therapy system, the positioning system comprising:

a linearly translatable tabletop arranged to linearly translate an imaging subject disposed on the tabletop to the imaging or therapy system;
a stationary couch supporting the linearly translatable tabletop, the stationary couch remaining stationary as the linearly translatable tabletop linearly translates an imaging subject disposed on the tabletop to the imaging or therapy system; and
an elongated position selector mounted on the stationary couch and remaining stationary with the stationary couch as the linearly translatable tabletop linearly translates an imaging subject disposed on the tabletop to the imaging or therapy system, the elongated position selector being elongated in a translation direction of the linearly translatable tabletop, the elongated position selector enabling selection of a position of a region of interest of the imaging subject along the linearly translatable tabletop by operating the elongated position selector at a position along the elongated position selector that coincides with the position of the region of interest, wherein the elongated position selector comprises:
a linear array of discrete selectors arranged parallel with the tabletop.

9. The positioning system as set forth in claim 8, further comprising:
storage for storing the selection of the position of the region of interest; and
a selector that, when selected, causes the current selection of the position of the region of interest to be stored in the storage.

10. The positioning system as set forth in claim 8, wherein the discrete selectors include sealed membrane push-buttons.

11. The positioning system as set forth in claim 8, wherein the discrete selectors are electrically interconnected such that selection of one of the discrete selectors deselects the other discrete selectors.

12. The positioning system as set forth in claim 8, wherein the elongated position selector has a length in the direction of elongation of at least 0.3 meter.

13. The positioning system as set forth in claim 8, wherein the elongated position selector has a length in the direction of elongation of at least 0.7 meter.

14. The positioning system as set forth in claim 8, wherein the elongated position selector has a length in the direction of elongation of at least one meter.

\* \* \* \* \*